United States Patent [19]

Kittelson

[11] 4,140,005

[45] Feb. 20, 1979

[54] METHOD AND INSTRUMENT FOR CONTINUOUS MONITORING OF AEROSOLS

[75] Inventor: David B. Kittelson, St. Paul, Minn.

[73] Assignee: The Regents of the University of Minnesota, Minneapolis, Minn.

[21] Appl. No.: 780,006

[22] Filed: Mar. 22, 1977

[51] Int. Cl.² ............................................. G01N 27/00
[52] U.S. Cl. ............................................. 73/28; 55/270
[58] Field of Search ..................... 73/23, 28, 432 PS; 23/232 E, 254 E; 55/101, 105, 123, 270; 356/187

[56] References Cited

U.S. PATENT DOCUMENTS

| | | | |
|---|---|---|---|
| 2,556,832 | 6/1951 | Vollrath | 55/270 |
| 2,730,005 | 1/1956 | Vonnegut | 73/28 |
| 3,473,118 | 10/1969 | Tassicker et al. | 73/28 |
| 3,520,172 | 7/1970 | Liu et al. | 73/28 |
| 3,763,428 | 10/1973 | Preist | 73/28 |
| 3,954,428 | 5/1976 | Marple et al. | 73/28 |

*Primary Examiner*—Stephen A. Kreitman
*Attorney, Agent, or Firm*—Burd, Braddock & Bartz

[57] ABSTRACT

A method and instrument for continuous monitoring of an aerosol as the sulfur content of atmospheric aerosols. The instrument has an electrostatic precipitator that is turned off and on at a given frequency to modulate the particle concentration of aerosol flowing through the precipitator. A total sulfur flame photometric detector sensitive to both gaseous and particulate sulfur receives a sample of the modulated aerosol from the precipitator. The modulated particle concentration of the aerosol supplied to the detector causes a fluctuating component in the detector output that is directly related to the sulfur particle concentration. This component is amplified by a frequency and phase sensitive lock-in amplifier tuned to the precipitator modulation frequency. The resulting output signal gives a continuous measure of the sulfur particle concentration entering the instrument.

64 Claims, 4 Drawing Figures

AEROSOL IN

EXCESS AEROSOL OUT

SAMPLE AEROSOL OUT

METHOD AND INSTRUMENT FOR CONTINUOUS MONITORING OF AEROSOLS

The Government has rights in this invention pursuant to Grant No. 6-9002 awarded by the U.S. Department of Commerce.

BACKGROUND OF INVENTION

Sulfur gases, and particles are common air pollutents. The measurement of air-borne particulate sulfur provides important data in air pollution monitoring and control. The common methods for measuring air-borne sulfur particulates are based on collections of sulfur particles on filters or impactors followed by chemical analysis of the resulting samples. Analysis techniques include: gravimetric analysis based on conversion to $BaSO_4$, $Ba(ClO_4)$ titrimetry, infrared attenuated total reflectance spectroscopy, ion chromatography, X-ray fluorescence spectroscopy, and X-ray photoelectron spectroscopy. All of these techniques depend on collections of samples followed by subsequent laboratory analysis. These methods utilize considerable periods of time and do not provide for continuous measurements of air-borne particles.

A semi-continuous sulfuric acid aerosol monitor has been developed. This monitor uses the same instrument to sample and make an analysis of the sampling. The monitor operates by collecting samples on Teflon filters and then volatilizing them into a dry $N_2$ stream flowing to a flame photometric detector. The sampling times are in the 15 to 30 minute range. The sulfur particles samples are collected on surfaces which are generally exposed to ambient sulfur gases. The possibility of conversion of some of the gaseous sulfur to particle form on these surfaces will produce erroneous results. Any collection surface subjected to atmospheric aerosols would become contaminated, and its collection and subsequent characteristics will change with time.

Methods which do not depend on collecting of particles on surfaces have been developed. A humidified nephelometer has been used to identify sulfuric acid aerosols. A temperature programmed heater at the inlet to a nephelometer has also been used to identify sulfuric acid aerosols. Both of these methods have analysis times of a few minutes.

Another technique to continuously monitor the sulfur aerosol uses a flame photometric monitor. A sulfur gas scrubber at the inlet to the monitor allows only sulfur particles to enter the flame. The particle concentration is directly measured. The output signal level of this instrument is barely above the flame background noise. In order to improve the signal to noise ratio, the sulfur particle must be integrated for several minutes. A filter is switched to the line for several minutes to obtain an integrated average background signal. The difference between the average non-filtered signal and the signal with the filter in line gives the signal component due to the sulfur particles. The total analysis time is approximately five minutes.

SUMMARY OF INVENTION

The invention is directed to a method and instrument operable to continuously detect aerosols without interference from gaseous pollutants. The instrument has an electrostatic precipitator powered by a pulsed high voltage power supply. The power supply is triggered to turn on and off by a reference signal from a lock-in amplifier. During the application of power to the precipitator the aerosol is collected in the precipitator. The pulsed modulated aerosol flows from the precipitator into a detector, as a flame photometric detector. The output from the detector has two components, a small modulated component and a large steady component. The modulated component is fed to the lock-in amplifier. The steady component relates to the gaseous sulfur in the sample. The amplifier is tuned to the frequency and phase of the signal output of the detector. The signal output from the lock-in amplifier can be read directly from a meter or can be connected to a recording device.

An object of the invention is to provide a method and instrument used to make a reliable and continuous measurements of aerosols, as sulfur, phosphorous, sodium and other metals, hydrocarbons, and nitrogen compounds. Another object of the invention is to provide an instrument for continuous measurement of sulfur aerosols having applications in air pollution monitoring, environmental chemistry, and laboratory studies of sulfur aerosol. A further object of the invention is to provide a method and apparatus to continuously monitor particulate sulfur levels in real time under field conditions ranging from ambient levels of about 1 microgram per cubic meter of sulfate to source emission levels which may be as high as 50 micrograms per cubic meter. An additional object of the invention is to provide an electrostatic precipitator that has high collection efficiency, is easy to clean, and has short turn-on and turn-off times. These and other objects and advantages of the invention are embodied in the method and apparatus disclosed herein.

IN THE DRAWINGS

FIG. 2 is a longitudinal cross sectional view of the electrostatic precipitator of FIG. 1;

FIG. 3 is a sectional view taken along line 3—3 of FIG. 2 and;

FIG. 4 is a sectional view taken along line 4—4 of FIG. 2.

DETAILED DESCRIPTION OF PREFERED EMBODIMENT

Figure 1:
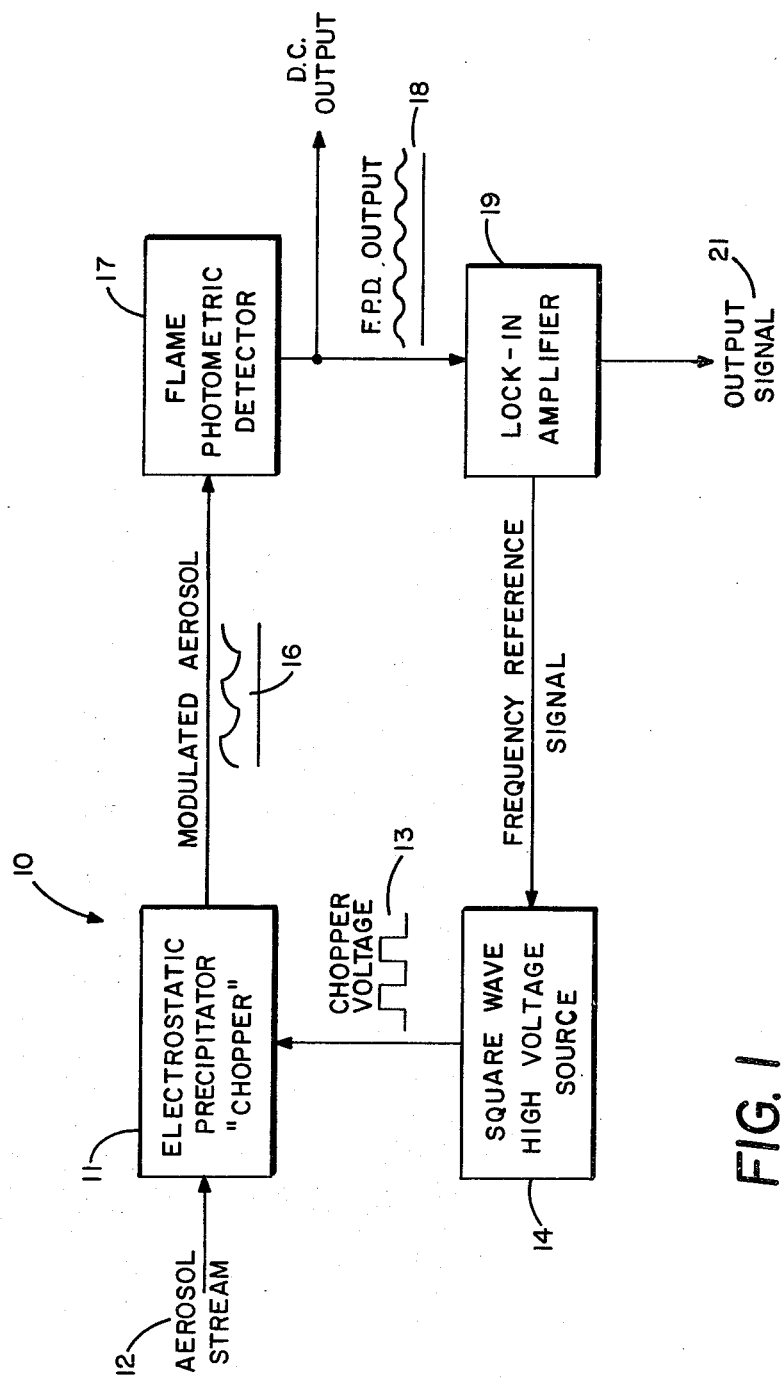
FIG. 1 is a block diagram of the pulsed electrostatic precipitation instrument of the invention.

The instrument is diagramatically illustrated in FIG. 1. The instrument, indicated generally at 10, has an electrostatic precipitator 11 receiving aerosol sample 12. Electrostatic precipitator 11 is sequentially energized or turned on and off by a high voltage square wave 13 emanating from a square wave high voltage source 14. When precipitator 11 is on, it charges and precipitates the particles removing them from the aerosol sample stream moving through the precipitator. When precipitator 11 is off, all the aerosol flows through the precipitator 11 and exits therefrom. A modulated aerosol 16 flows from precipitator 11. The modulated aerosol 16 flows into a flame photometric detector 17. Detector 17 can be a commercial Meloy SA 285 flame photometric detector. The modulated aerosol in the detector 17 results in a modulated output from the detector because the detector is sensitive to the aerosol. The modulated portion of the detector output signal is a function of the aerosol concentration in the sample.

Flame photometric output 18 is fed to lock-in amplifier 19. Amplifier 19 selectively amplifies the modulated a.c. component of the detector output signal at the frequency of the square wave high voltage source 14 applied to precipitator 11. Since precipitator 11 does not modulate any gas phase materials, the a.c. component depends primarily on the aerosol concentration of the sample. Gas phase sulfur content, for example, $SO_2$, is indicated by the d.c. component of the detector output. Thus, the instrument simultaneously measures gaseous and particle sulfur. The output signal 21 from amplifier 19 can be read directly from a meter (not shown) on the front of the amplifier or can be connected to a recording device. The output signal is a continuous measure of the sulfur particle concentration entering the instrument.

The instrument 10 has three main components: electrostatic precipitator 11, flame photometric detector 17, and lock-in amplifier 19. Aerosol sample 12 enters the instrument 10 through the electrostatic precipitator 11 and then flows into flame photometric detector 17. When precipitator 11 is off, both gaseous sulfur compounds and the sulfur particles pass through the precipitator 11 to the flame photometric detector 17 and produce an output response. When precipitator 11 is turned on, Only gaseous sulfur compounds pass through the precipitator 11 and are detected by flame photometric detector 17. Precipitator 11 is turned on and off at regular intervals whereby the amplitude of the pulsed component of the signal can be used as an indication of the sulfur gas concentration. Lock-in amplifier 19 is used to measure the amplitude of the pulsed component of flame photometric detector output signal 18. Amplifier 19 is synchronized to the signal 18 by both frequency and phase so that much of the random flame noise from detector 17 is rejected. A small a.c. signal is extracted from a fairly large and noisey d.c. signal.

Electrostatic precipitator 11, identified as a chopper, is characterized as having a high collection efficiency and short turn-on and turn-off times. Several types of precipitators can be used. The precipitator can have a common charging and collection region or separate charging and collecting regions. One type of precipitator is shown as 22 in FIGS. 2, 3, and 4.

Electrostatic precipitator 22 has an elongated cylindrical body or casing 23 having a longitudinal chamber 24. A tubular inlet member 26 is mounted on the top of body 23. The lower portion of member 26 fits into the upper end of chamber 24 and is held in assembled relation with body 23 with a cap 27. The plurality of screws 28 secure cap 27 to the top of body 23. An elongated metal cylinder, tube or sleeve 29 is concentrically positioned within tubular member 26. Cylinder 29 has an inside cylindrical surface 31 providing a particle collection surface. A plurality of holding bolts 32 threaded into body 23 engage the lower portion of cylinder 29 to mount cylinder 29 on body 23. Cylinder 29 has an inlet or mouth 33 leading to an elongated passage or charging and collection region 34. Passage 34 has a uniform diameter throughout its length and is surrounded by the cylindrical particle collecting surface 31.

An elongated wire 36 is located along the longitudinal central axis of metal cylinder 29. Wire 36 is a fine, 25 μm diameter tungsten wire. The upper or inlet end of wire 36 is attached to an insulator wire 37. Insulator wire 37 is mounted on a bridge or support 38, positioned in tubular member 26 adjacent mouth 33. A high voltage connector 39 is mounted on the mid portion of body 23. The lower end of wire 36 is secured to the end of connector 39 extended into chamber 24. In use a high negative voltage of about −2200V is applied to wire 39 to produce a corona discharge. The aerosol particles flowing through passage 34 are charged by the negative ions produced and are precipitated onto cylindrical surface 31 by the high electric field existing between wire 36 and the grounded metal cylinder 29.

When the voltage is turned off, the aerosol particles flow or penetrate through the passage 34 without being precipitated.

A center line means is used to extract a portion of the modulated aerosol in chamber 24. About 10% of the aerosol is collected by the center line means. The center line means comprises an isokinetic tubular probe 42 extended upwardly into chamber 24. Probe 42 has a passage 43 for carrying the modulated aerosol from chamber 24 to flame photometric detector 17. A plate 44 secured to probe 42 is used to mount the probe on the bottom of body 23. A plurality of screws 46 secure plate 44 to body 23. The remaining 90% of the aerosol flow in chamber 24 is not used. It is discharged to the atmosphere via a side bore 47 in body 23 and a tubular hose connector 48 mounted on body 23. Bore 47 is open to the bottom of chamber 24. Probe 42 extends into chamber 24 along the central longitudinal axis of the chamber. Probe 42 exit ends beyond the second passage 47 locating the inlet end upstream from the inlet of passage 47. A filter (not shown) can be used to remove the aerosols from the excess gases and aerosols.

Tests of the efficiency of electrostatic precipitator 22 in the 0.01 to 1 μm particle diameter range show that it has nearly 100% collection efficiency at an applied voltage of −2200V on corona wire 36.

The operation of a specific embodiment of instrument 10 is described as follows. The specific embodiment includes the electrostatic precipitator 22, a Meloy SA 285 flame photometric detector 17, and a Princeton Applied Research lock-in amplifier 19. The aerosol sample flows into the tubular member 26 into passage 34 of metal cylinder 29. The power from the square wave high voltage source 14 is applied to connector 39 thereby supplying a high voltage to wire 36. Preferably, a high voltage of −2200V is applied to wire 36 to produce a corona discharge. The square wave high voltage source 14 is operated at approximately 2.2 kV. The aerosols moving through passage 34 are charged with negative ions produced by the corona discharge. These charged particles are precipitated onto the cylindrical inside surface 31 of the metal cylinder 29. The gaseous components are not charged and flow through the passage 34 into chamber 24. The square wave high voltage source 14 is sequentially triggered by the reference signal from the lock-in amplifier 19 to intermitently supply power to precipitator 22. When the voltage is turned off, the aerosol particles in passage 34 can flow through the passage 34 without being precipitated on the metal cylinder 29. The result is that there is a modulated aerosol sample in chamber 24. A portion of the aerosol sample in chamber 24 moves through passage 43 of probe 42 to the flame phtotmetric detector 17. Preferably, about 10% of the sample in chamber 24 is suppled to detector 17. The remaining 90% exits to the atmosphere via the side bore 47. A filter (not shown) can be used before the aerosol is discharged back into the atmosphere.

The modulated or pulsed aerosol 16 flows from precipitator 22 into the flame photometric detector 11. The flame photometric detector 17 operates to detect both gases and particulate sulfur. The detector output 18 has a data signal as to the total sulfur content of the aerosol sample into the detector. The modulated aerosol 16 moving into the detector 17 causes the detector output signal 18 to fluctuate since it is related directly to the sulfur content of the aerosol. The fluctuating component of detector 17 is directly related to the sulfur particle concentration. This component is amplified by the frequency and phase sensitive lock-in amplifier 19. Amplifier 19 is tuned to the precipitator modulation frequency with the result that the amplifier output signal 21 is a continuous measure of sulfur particle concentration entering instrument 10.

Amplifier 19 is a commercially available lock-in amplifier. The frequency rate is 0.2 HZ. This frequency is used because it is compatible with the frequency response of flame photometric detector 17. Higher frequencies can be used with detectors having faster responses. The faster detectors will allow higher chopping frequencies which result in better signal to noise ratios and overall instrument response.

Instrument 10 herein described is operable to detect sulfur aerosols. Other types of detectors can be used in lieu of detector 17 to measure other types of aerosols, for example, the following aerosols can be measured: phosphorous by flame photometry, sodium and other metals by flame photometry, hydrocarbons by flame ionization and nitrogen compounds by flame ionization. The main detector characteristic is that it should have a fairly quick response to particles containing the material to be monitored. Detector time constants of less than about 10 seconds are desireable.

While there has been shown and described a prefered embodiment of the instrument and method of continuously monitoring atmospheric aerosols it is understood that modifications, changes in the precipitator, detector, and amplifier can be made by those skilled in the art without departing from the invention.

The invention is defined in the following claims:

1. An instrument for continuous monitoring of an aerosol having a particle concentration comprising: an electrostatic precipitator for accommodating a flowing gas including an aerosol having a particle concentration, power source means connected to the precipitator operable to turn the precipitator on and off at a selected frequency to modulate the particle concentration of the aerosol, said particles being removed from the flowing gas when the precipitator is on and said particles allowed to flow with the gas when the precipitator is off, detector means for receiving the modulated aerosol, said detector means being sensitive to the modulated aerosol to produce a fluctuating output signal related to the particle concentration of the aerosol, and amplifier means for amplifying the fluctuating output signal to provide an output signal related to the particle concentration of the aerosol.

2. The instrument of claim 1 wherein: said precipitator includes a body having a chamber, metal tube means mounted on the body, said tube means having an inlet end for receiving an aerosol, an outlet end open to the chamber, and an inside surface surrounding a passage for carrying the gas and aerosol from the inlet end to the outlet end, a wire extended longitudinally through said passage, and outlet means having at least one outlet passage open to the chamber for carrying the modulated aerosol out of the chamber, said power means being operatively connected to said wire whereby said wire accommodates a voltage to establish a corona discharge thereby charging the aerosol in the passage, said charged aerosol being collected on the inside surface of the tube means.

3. The instrument of claim 2 wherein: the metal tube means is a cylindrical tube having a cylindrical inside surface.

4. The instrument of claim 2 wherein: a tubular member is mounted on the body, said tube means having a portion located in the tubular member.

5. The instrument of claim 4 wherein: a support is located in the tubular member adjacent the inlet end of the tube means, said wire having a first end connected to the support to locate the wire along the central longitudinal axis of the passage.

6. The instrument of claim 5 wherein: a connector is mounted on the body and projected into the chamber adjacent the outlet end of the tube means, said wire having a second end connected to the connector, said means for applying a voltage to the wire being coupled to the connector.

7. The instrument of claim 2 wherein: the outlet means comprises a first outlet having a first outlet passage open to the chamber for carrying a portion of the aerosol out of the chamber, and a second outlet having a second passage open to the chamber for carrying the remainder of the aerosol out of the chamber.

8. The instrument of claim 7 wherein: the first outlet is an isokinetic probe having an inlet end extended into the chamber along the longitudinal axis thereof.

9. The instrument of claim 8 wherein: the probe extends to the chamber beyond the second passage.

10. The instrument of claim 1 wherein: the power source means is a square wave high voltage source.

11. The instrument of claim 1 wherein: the amplifier means is a lock-in amplifier tuned to the on and off frequency of the precipitator.

12. The instrument of claim 11 wherein: the power source means is a square wave high voltage source.

13. An instrument for modulating an aerosol comprising:
an electrostatic precipitator for accommodating a flowing gas including an aerosol, said precipitator including gas inlet means thereto and outlet means therefrom, said outlet means including a first outlet open to the precipitator for carrying a sampled portion of the aerosol therefrom and a second outlet communicating with the precipitator for carrying the remainder of the aerosol outwardly therefrom for determination of particle concentration of the aerosol, and power source means connected to the precipitator operable to turn the precipitator on and off at a selected frequency to modulate the aerosol, said aerosol being removed from the flowing gas when the precipitator is on and said aerosol allowed to flow with the gas when the precipitator is off towards said first and second outlets.

14. The instrument of claim 13 wherein:
said precipitator includes a body having a chamber, metal tube means mounted on the body, said tube means having an inlet end for receiving an aerosol, said outlet means open to the chamber, and an inside surface surrounding a package for carrying the gas and aerosol from the inlet end to the outlet means, a wire extended longitudinally through said passage, said power means being operatively connected to said wire whereby said wire accommodates a voltage to establish a corona discharge thereby charging the aerosol in the passage, said charged aerosol being collected on the inside surface of the tube means.

15. The instrument of claim 14 wherein: the metal tube means is a cylindrical tube having a cylindrical inside surface.

16. The instrument of claim 15 wherein: a tubular member is mounted on the body, said tube means having a portion located in the tubular member.

17. The instrument of claim 16 wherein: a support is located in the tubular member adjacent the inlet end of the tube means, said wire having a first end connected to the support to locate the wire along the central longitudinal axis of the passage.

18. The instrument of claim 17 wherein: a connector is mounted on the body and projected into the chamber adjacent the outlet means of the tube means, said wire having a second end connected to the connector, said means for applying a voltage to the wire being coupled to the connector.

19. The instrument of claim 13 wherein: the first outlet is an isokinetic probe having an inlet end extended into the chamber along the longitudinal axis thereof.

20. The instrument of claim 19 wherein: the probe extends to the chamber beyond the second passage.

21. The instrument of claim 13 wherein: the power source means is a square wave high voltage source.

22. A method of continuous monitoring of an aerosol having a particle concentration comprising: modulating the particle concentration of an aerosol flowing with a gas with an electrostatic precipitator by alternatively removing the particles from the flowing gas and allowing the particles to flow with the gas, supplying the modulated aerosol to a detector sensitive to the modulated aerosol to produce a fluctuating output signal, and amplifying the fluctuating output signal to provide an output signal related to the particle concentration of the aerosol.

23. The method of claim 22 wherein: the aerosol has gaseous end particle sulfur content which is monitored, said detector comprising a flame photometric detector sensitive to gaseous and particle sulfur whereby the modulated output signal of the detector is related to the sulfur particle concentration of the aerosol.

24. The method of claim 22 wherein: the aerosol is modulated by turning the electrostatic precipitator on and off at a selected frequency.

25. The method of claim 22 wherein: the aerosol is moved through a passage and modulated in said passage by turning the precipitator on and off.

26. The method of claim 22 wherein: only a portion of the modulated aerosol is supplied to the detector.

27. The method of claim 22 wherein: the fluctuating output signal is amplified with a lock-in amplifier tuned to the modulating frequency of the precipitator.

28. The method of claim 29 wherein: the aerosol has gaseous and particle sulfur content which is monitored, said detector comprising a flame photometric detector sensitive to gaseous particle sulfur whereby the modulated output signal of the detector is related to the sulfur particle concentration of the aerosol.

29. A method of monitoring an aerosol having a particle concentration comprising: modulating the particle concentration of an aerosol flowing with a gas by alternatively removing particles from the gas and allowing particles to flow with the gas, supplying the gas carrying the modulated particle concentration of the aerosol to a means sensitive to the modulated particle concentration to produce a fluctuating output signal, and amplifying the fluctuating output signal to provide an output signal related to the particle concentration of the aerosol.

30. The method of claim 29 wherein: only a portion of the modulated particle concentration is supplied to the means sensitive to the particle concentration.

31. The method of claim 29 wherein: the aerosol has a gaseous and particle sulfur content, said means sensitive to the modulated particle concentration being sensitive to gaseous and particle sulfur and having a modulated output signal relating to particle sulfur concentration and an unmodulated output related to gaseous sulfur.

32. The method of claim 31 wherein: only a portion of the modulated particle sulfur concentration is supplied to the means sensitive to the particle sulfur concentration.

33. The method of claim 29 wherein: the aerosol has a particle phosphorous content, said means sensitive to the modulated particle concentration being sensitive to particle phosphorous whereby the modulated output signal is related to the particle phosphorous concentration of the aerosol.

34. The method of claim 29 wherein: the aerosol has a particle hydrocarbon content, said means sensitive to the modulated particle concentration being sensitive to particle hydrocarbons whereby the modulated output signal is related to the particle hydrocarbon concentration of the aerosol.

35. An instrument for monitoring an aerosol having a particle concentration comprising: first means for accommodating a flowing gas including an aerosol having a particle concentration, said first means being operable to remove said particles from the flowing gas and allowing said particles to flow with the gas, second means connected to the first means operable to turn the first means on and off at a selected frequency to modulate the particle concentration of the aerosol, said particles being removed from the flowing gas when the first means is on and said particles allowed to flow with the gas when the first means is off, detector means for receiving the modulated aerosol, said detector means being sensitive to the modulated aerosol to produce a fluctuating output signal, an amplifier means for amplifying the fluctuating output signal to provide an output signal related to the particle concentration of the aerosol.

36. The instrument of claim 35 wherein: the first means is an electrostatic precipitator.

37. The instrument of claim 36 wherein: the second means is a power source connected to the precipitator to turn the precipitator on and off at a selected frequency.

38. The instrument of claim 35 wherein: the amplifier means is a locked-in amplifier tuned to the on-off frequency of the first means.

39. The instrument of claim 38 wherein: the second means is a power source means having a square wave high voltage source.

40. The instrument of claim 35 wherein: said aerosol has a particle sulfur content, the detector means is a flame photometric detector sensitive to particulate sulfur whereby the modulated output signal of the detector is related to the particle sulfur concentration of the aerosol.

41. The instrument of claim 35 wherein: the detector means is a flame ironization detector sensitive to hydrocarbon aerosols.

42. The instrument of claim 35 wherein: the detector means is a flame photometric detector.

43. An instrument for continuous monitoring of an aerosol having a gaseous and particle sulfur content comprising: an electrostatic precipitator for accommodating an aerosol having a gaseous and particle sulfur content, power source means connected to the precipitator operable to turn the precipitator on and off at a selected frequency to modulate the particle sulfur content of the aerosol, detector means for receiving the modulated aerosol, said detector means being sensitive to the modulated aerosol to produce a fluctuating output signal, said detector means being a flame photometric detector sensitive to gaseous and particle sulfur whereby the modulated output signal of the detector is related to the sulfur particle concentration of the aerosol, and amplifier means for amplifying the fluctuating output signal to provide an output signal related to the sulfur particle content of the aerosol.

44. The instrument of claim 43 wherein: the flame photometric detector has an unmodulated output signal that is related to the gaseous portion of the aerosol.

45. The instrument of claim 43 wherein: said precipitator includes a body having a chamber, metal tube means mounted on the body, said tube means having an inlet end for receiving an aerosol, an outlet end open to the chamber, and an inside surface surrounding a passage for carrying the gas and aerosol from the inlet end to the outlet end, a wire extended longitudinally through said passage, and outlet means having at least one outlet passage open to the chamber for carrying the modulated aerosol out of the chamber, said power means being operatively connected to said wire whereby said wire accommodates a voltage to establish a corona discharge thereby charging the aerosol in the passage, said charged aerosol being collected on the inside surface of the tube means.

46. The instrument of claim 45 wherein: the metal tube means is a cylindrical tube having a cylindrical inside surface.

47. The instrument of claim 45 wherein: a tubular member is mounted on the body, said tube means having a portion located in the tubular member.

48. The instrument of claim 47 wherein: a support is located in the tubular member adjacent the inlet end of the tube means, said wire having a first end connected to the support to locate the wire along the central longitudinal axis of the passage.

49. The instrument of claim 48 wherein: a connector is mounted on the body and projected into the chamber adjacent the outlet end of the tube means, said wire having a second end connected to the connector, said means for applying a voltage to the wire being coupled to the connector.

50. The instrument of claim 45 wherein: the outlet means comprises a first outlet having a first outlet passage open to the chamber for carrying a portion of the aerosol out of the chamber, and a second outlet having a second passage open to the chamber for carrying the remainder of the aerosol out of the chamber.

51. The instrument of claim 50 wherein: the first outlet is an isokinetic probe having an inlet end extended into the chamber along the longitudinal axis thereof.

52. The instrument of claim 51 wherein: the probe extends to the chamber beyond the second passage.

53. The instrument of claim 43 wherein: the power source means is a square wave high voltage source.

54. The instrument of claim 43 wherein: the amplifier means is a lock-in amplifier tuned to the on and off frequency of the precipitator.

55. The instrument of claim 54 wherein: the power source means is a square wave high voltage source.

56. An instrument for continuous monitoring of an aerosol having gaseous and particle sulfur content comprising: an electrostatic precipitator for accommodating an aerosol having a gaseous and particle sulfur content, power source means connected to the precipitator operable to turn the precipitator on and off at a selected frequency to modulate the particle sulfur content of the aerosol, said power source having a square wave high voltage source, detector means for receiving the modulated aerosol, said detector means being sensitive to the modulated aerosol to produce a fluctuating output signal, said detector means being a flame photometric detector sensitive to gaseous and particle sulfur whereby the modulated output signal of the detector is related to the sulfur particle concentration of the aerosol and the unmodulated output signal of the detector is related to the gaseous portion of the aerosol, and amplifier means for amplifying the fluctuating output signal to provide an output signal related to the sulfur particle content of the aerosol, said amplifier means being a locked-in amplifier tuned to the on-off frequency of the precipitator.

57. The instrument of claim 56 wherein: said precipitator includes a body having a chamber, metal tube means mounted on the body, said tube means having an inlet end for receiving an aerosol, an outlet end open to the chamber, and an inside surface surrounding a passage for carrying the gas and aerosol from the inlet end to the outlet end, a wire extended longitudinally through said passage, and outlet means having at least one outlet passage open to the chamber for carrying the modulated aerosol out of the chamber, said power means being operatively connected to said wire whereby said wire accommodates a voltage to establish a corona discharge thereby charging the aerosol in the passage, said charged aerosol being collected on the inside surface of the tube means.

58. The instrument of claim 57 wherein: the metal tube means is a cylindrical tube having a cylindrical inside surface.

59. The instrument of claim 57 wherein: a tubular member is mounted on the body, said tube means having a portion located in the tubular member.

60. The instrument of claim 59 wherein: a support is located in the tubular member adjacent the inlet end of the tube means, said wire having a first end connected to the support to locate the wire along the central longitudinal axis of the passage.

61. The instrument of claim 60 wherein: a connector is mounted on the body and projected into the chamber adjacent the outlet end of the tube means, said wire having a second end connected to the connector, said means for applying a voltage to the wire being coupled to the connector.

62. The instrument of claim 56 wherein: the outlet means comprises a first outlet having a first outlet passage open to the chamber for carrying a portion of the aerosol out of the chamber, and a second outlet having a second passage open to the chamber for carrying the remainder of the aerosol out of the chamber.

63. The instrument of claim 62 wherein: the first outlet is an isokinetic probe having an inlet end extended into the chamber along the longitudinal axis thereof.

64. The instrument of claim 63 wherein: the probe extends to the chamber beyond the second passage.

* * * * *